United States Patent [19]
Prota et al.

[11] Patent Number: 6,160,127
[45] Date of Patent: Dec. 12, 2000

[54] PROCESS FOR THE PREPARATION OF SUBSTITUTED INDOLES

[75] Inventors: Giuseppe Prota, Naples, Italy; Gottfried Wenke, Woodbridge, Conn.

[73] Assignee: Bristol-Myers Squibb Company, New York, N.Y.

[21] Appl. No.: 09/115,427

[22] Filed: Jul. 15, 1998

[51] Int. Cl.[7] .................. C07D 209/04; C07D 209/12
[52] U.S. Cl. ................ 548/508; 548/490; 548/491
[58] Field of Search .................... 548/508, 490, 548/491

[56] References Cited

U.S. PATENT DOCUMENTS

| | | | |
|---|---|---|---|
| 2,934,396 | 4/1960 | Charle et al. | 8/88 |
| 3,194,734 | 7/1965 | Seemuller et al. | 167/88 |
| 4,808,190 | 2/1989 | Grollier et al. | 8/423 |
| 5,262,546 | 11/1993 | Pan et al. | 548/508 |
| 5,704,949 | 1/1998 | Prota et al. | 8/423 |

FOREIGN PATENT DOCUMENTS 3737825  5/1988  Germany .

OTHER PUBLICATIONS

Mason, H.S., The Chemistry of Melanin, 172, 83(1948).
Pawelek, John M., et. al., 5,6–Dihydroxyindole is a Melanin Precursor showing potent cytotoxicity, Nature 276, 627(1978).
Beer, R.J.S., et al., The Chemistry of Melanins, Part I. The Synthesis of 5,6–Dihydroxyindole and Related Compounds, J. Chem. Soc. (1948) 2223.
Benigni, J.D., et al., The Synthesis of 5,6–Dihydroxyindole and Some of its Derivatives, J. Heterocycl. Compd., 1965, 2, 387.
Sinhababu, A.K., et al, Silica Gel Assisted Reductive Cyclization of Alkoxy–2, B–dinitrostyrenes to Alkoxyindoles, J. Org. Chem., vol. 48, No.19, 1983, 3347.
Murphy, Brian P., Efficient Synthesis of 5,6–Diacetoxyindole: A Stable Eumelanin Precursor, J. Org. Chem. 1985, 5873.
Murphy, Brian P. et al., Synthesis of 5,6–Dihydroxyindole: A Novel Reductive Cyclization of (E)–4,5–Dihydroxy–2, B–Dinitrostyrene, Synthetic Communications, 15 (4), 321 (1985).
Murphy, Brian P., Synthesis and Physical Properties of 5,6–Dihydroxyindole, J. Org. Chem. 1985, 50, 2790.
Batcho, A.D., et al., Indoles From 2–methylnitrobenzenes By Condensation with Formamide Acetals Followed by Reduction: 4 Benzyloxyindole, Organic Syntheses Coll., vol. VII p.34 (1990).

*Primary Examiner*—Joseph K. McKane
*Assistant Examiner*—Jane C. Osowecki
*Attorney, Agent, or Firm*—Charles J. Zeller; Morton S. Simon

[57] ABSTRACT

A process for the preparation of 5,6-disubstituted indoles in which a 4-5-disubstituted-2,β-nitrostyrene is subjected to a reductive cyclization in the presence of a water soluble dithionite salt.

19 Claims, No Drawings

PROCESS FOR THE PREPARATION OF SUBSTITUTED INDOLES

FIELD OF THE INVENTION

The present invention relates to a process for the synthesis of substituted indoles by the reductive cyclization of substituted-2β-dinitrostyrenes.

BACKGROUND OF THE INVENTION 5,6-Dihydroxy indole is well known as playing an important role in the production of the organic pigment melanin. This compound also appears to be involved in the process for the formation of eumelanins from, 3,4-dihydroxyphenylalanine [J. Biol. Chem. 172, 83 (1948); Nature, 276,627 (1978)].

5,6-Dihydroxyindole (DHI) and derivatives thereof have been described and used in dye compositions for dyeing keratinous fibers, and especially human hair. See, for example, U.S. Pat. No. 4,808,190, U.S. Pat. No. 5,704,949, U.S. Pat. No. 3,194,734 and U.S. Pat. No. 2,934,396.

5,6-Diacetoxyindole (DAI) has been obtained by reductive cyclization of 4,5-diacetoxy-2,β-dinitrostyrene with Fe in acetic acid. For the reduction of 2 g of this material to DAI, 10 g of Fe, 40 ml of acetic acid and 50 ml of absolute alcohol were required. In addition, for isolation of DAI from the reaction mixture, several extractions with ether (at least 5 times) and recrystallization were necessary.

Isolation of DHI required additional steps after hydrolysis of DAI. (R. J. Beer, K. Clarke, H. G. Khorana, A. Robertson The Chemistry of the Melanins. Part I, The Synthesis of 5,6-Dihydroxyindole and related compounds. *J. Chem. Soc.,* 1948, 2223)

5,6-Dibenzyloxyindole (DBI) has been produced by reductive cyclization of 4,5-dibenzyloxy-2,β-dinitrostyrene with Fe in acetic acid as in Beer et al, supra. 4-5-dibenzyloxy-2,β-dinitrostyrene was made by nitration of 3,4-benzyloxy-β-nitrostyrene.

DHI has been obtained from DBI by hydrogenation in the presence of Pd/C. (J. D. Benigni, R. L. Minnis: The synthesis of 5,6-dihydroxyindole and some of its derivatives, *J. Heterocycl, Compd.,* 1965, 2, 387).

The disadvantages of this synthesis are the same as in Beer et al., supra, since no improvement is made in the reductive cyclization step.

DBI has been obtained by silica gel assisted reductive cyclization of 4,5-dibenzyloxy-2,β-dinitrostyrene. A minimum of 1.5 g of silica gel per mmole of 4,5-dibenzyloxy-2,β-dinitrostyrene are required. (A. K. Sinhababu and R. T. Borchardt: Silica gel assisted reductive cyclization of alkoxy-2,β-dinitrostyrenes to alkoxyindoles, *J. Org. Chem.* 1983, 3347). The method is expensive and difficult to perform on a large scale.

DAI has been produced by reductive cyclization of 4,5-dibenzyloxy-2,β-dinitrostyrene with 5% Pt/C in acetic acid followed by acetylation. The whole process required 5 operations and HPLC was used to purify the final compound DAI. (B. P. Murphy, Efficient synthesis of 5,6-diacetoxyindole: A stable eumelanin precursor. *J. Org. Chem.* 1985, 5873)

DAI has been obtained from 4,5-dihydroxy-2,β-dinitrostyrene by hydrogenation of an aqueous dispersion over 10% Pd/C.

4,5-dihydroxy-2,β-dinitrostyrene was obtained from 4,5-dibenzyloxy-2,β-dinitrostyrene by refluxing with $CF_3CO_2H$ for three hours in argon atmosphere: (B. P. Murphy, H. D. Banks, Synthesis of 5,6-dihydroxyindole: A novel reductive cyclization of (E)-4,5-dihydroxy-2,β-dinitrostyrene. *Synthetic Commun.* 15(4), 1985, 321; B. P. Murphy, T. M. Schultz. Synthesis and physical properties of 5,6-dihydroxyindole. *J. Org. Chem.* 1985, 50, 2790).

DAI has been obtained from 2-methyl-4,5-dibenzyloxy-nitrobenzene by condensation with N,N-dimethylformamide acetals and reduction with Raney nickel catalyst. This method requires protection of the phenolic groups and somewhat expensive reagents and catalysts (A. D. Batcho, W. Leimgruber, Organic Syntheses Coll. Vol. VII, 1990).

DHI has been produced by hydrogenation of 2-nitro-4,5-dihydroxybenzyl cyanide with Pd/C. Synthesis of 2-nitro-4,5-dihydroxybenzyl cyanide requires 4 steps from 3,4-dimethoxybenzyl cyanide: (DE 3737825 A1 L'Oreal, Paris Fr (May 1988)).

DAI has been obtained from trans-4,5-dibenzyloxy-β-pyrrolidino-2-nitrostyrene by a "one pot" method. Synthesis of trans-4,5-dibenzyloxy-β-pyrrolidino-2-nitrostyrene is performed as described in Batcho et al, supra. (U.S. Pat. No. 5,262,546, (November 1993)).

Known preparative processes do not enable 5,6-disubstituted indoles to be prepared in a satisfactory manner, especially on an industrial scale.

The pivotal step in the synthesis of DHI (or DHI derivatives) is the final reductive cyclization and isolation of the product. Prior art methods require use of precious metal catalysts or high pressure hydrogenation.

It is an object of the present invention to provide a process which is inexpensive, simple to perform (without the need for special equipment) and more easily scaled-up than prior art processes.

SUMMARY OF THE INVENTION

The instant invention relates to a process for the preparation of substituted indoles from substituted-2,β-dinitrostyrenes of the formula I

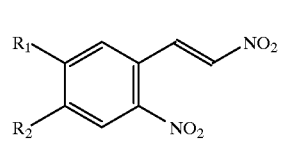

in which $R_1$ and $R_2$ each independently denotes hydrogen, acyloxy, benzyloxy or hydroxy with the proviso that $R_1$ and $R_2$ are not both hydrogen. The cyclization reaction is accomplished through the use of a dithionite salt. Preferred dithionite salts are water soluble salts. Useful dithionite salts include alkali metal or alkaline earth metal dithionites and zinc dithionite. The metal dithionite should not react with the substituted indole so as to appreciably reduce the yield of the indole.

DETAILED DESCRIPTION OF THE INVENTION

The present invention provides a new route to substituted indoles of the formula (II):

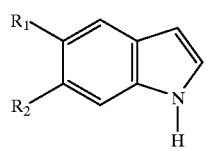

from substituted-2,β-dinitrostyrene (I) using a reductive cyclization in a suitable reaction medium. Preferably, the present invention relates to the preparation of disubstituted indoles from 4,5-disubstituted-2,β-dinitrostyrene.

The overall reaction scheme starting with the 3,4-disubstituted benzaldehyde (III) is shown in Scheme (I):

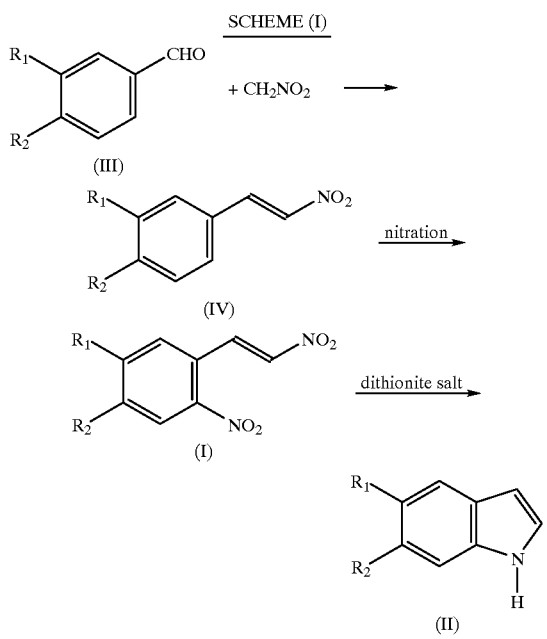

In the compounds of formulas I and II, $R_1$ and $R_2$ are each independently hydrogen, acyloxy, benzyloxy or hydroxy, preferably, $C_1$–$C_3$-acyloxy, optionally substituted benzyloxy or hydroxy, more preferably, acetoxy, benzyloxy or hydroxy with the proviso that $R_1$ and $R_2$ are not both hydrogen.

The reaction to form compounds (IV) is a known reaction whose conditions would be determinable by the ordinary artisan. Similarly, the reaction to form compounds (I) where $R_1$ and $R_2$ are acyloxy or benzyloxy is a known reaction whose conditions are determinable by the ordinary artisan. In the case where $R_1$ and $R_2$ are acyloxy, the acyloxy groups deactivate the aromatic ring towards nitration. More rigorous conditions may be needed or the acyl groups can be added after nitration. However, the prior art reaction to form compound I where R, and $R_2$ are both hydroxy has not been possible by use of prior reaction conditions. It was thought that the hydroxy groups needed to be protected, i.e., converted to a group such as benzyloxy group before nitration can be carried out. It has been found by applicants that the reaction to form 3,4-dihydroxy nitrostyrene (I) can be carried out directly, i.e., without the need for protection and deprotection of the hydroxyl groups. The nitration can be carried out in a polar organic solvent with tetranitromethane in the presence of a water soluble zinc salt. Useful zinc salts include, for example, zinc sulfate and zinc chloride, zinc nitrate (provided that the anion is compatible with reaction product). It is preferred that the reaction mixture be buffered to be mildly or slightly alkaline, i.e. pH 8–9 and the nitration is carried out with cooling, preferably at about –5° to about 10° C.

The important condition for carrying out this nitration is the use of a water soluble zinc salt. It is believed that the zinc ion may act as a labile protecting group by chelating with the hydroxyl groups of the catechol during the nitration reaction provided that the pH of the reaction mixture is mildly alkaline. It is also important to use tetranitromethane as the nitrating agent. This compound has been found to nitrate the catechol compound in alkaline medium to give the desired compound(s) in acceptable yield.

It should be noted that in the case of non-catechol compounds, the usual nitrating agents such as, for example, nitric acid, can be used. A possible nitration reaction of the non-catechol compounds can be carried out in the presence of nitric acid.

Typical but not limiting conditions for non-catechol compounds are as follows. The condensation reaction to form the nitrostyrene (IV) can be carried out at atmospheric pressure in a solution of ammonium acetate in acetic acid, preferably at reflux although this reaction will proceed at lower temperatures. When R is benzyloxy the nitrostyrene (IV) is only slightly soluble in the reaction medium at ambient temperature and the precipitate can be recovered by filtration.

After recovery of the non-catechol nitrostyrene (IV), this compound can be nitrated with fuming nitric acid, according to known procedures, to produce the 4,5-disubstituted-2,β-dinitrostyrene (I). The synthesis of the nitro derivatives, when R is benzyloxy, is described in greater detail by Benigni and Minnis, J. Heterocycl. Compounds, 1965, Vol. 2, p. 387, et seq.

The dinitrostyrene derivative (I) is subjected to reductive cyclization using a metal water soluble dithionite, such as an alkali metal or alkaline earth metal dithionite or zinc dithionite. Dithionites useful in this reaction include, for example, sodium dithionite, potassium dithionite, magnesium dithionite, calcium dithionite or zinc dithionite, preferably, sodium dithionite. An aqueous solution of the dithionite salt in an aqueous buffer having a pH of from about 3 to about 7, or in some case an alkaline pH of up to about 9 or 10, for example when $R_1$ or $R_2$ are benzyloxy as in example 6, containing the dinitrostyrene (1) is stirred in an inert atmosphere. After the reaction is completed, the pH of the reaction mixture is adjusted to the acidic range and the mixture is extracted with an organic solvent such as those known to those skilled in the art. The combined organic solvent layers containing the disubstituted indole are washed and dried and the product can be precipitated from solution by the addition of a non-polar organic solvent.

In general, the reductive cyclization can be carried out in polar, hydroxyl group-containing solvents such as water, lower alkanols, lower aliphatic carboxylic acids or mixtures thereof Examples of lower alkanols include methanol, ethanol, isopropanol, n-butanol, etc. Examples of useful carboxylic acids include acetic acid, proprionic acid, etc. These polar solvents can be used individually or in mixtures of two or more at any proportion in which they are mutually soluble under reaction conditions. A two-phase solvent system comprising water and a non-polar organic solvent can be used in the case of diacyloxy nitrostyrenes. The preferred reaction medium for optimum yield depends upon the definition of $R_1$ and $R_2$ in formula II.

At the completion of the reaction, the reaction system may be acidified to a pH of about 5 or less by the addition of acid such as, for example, HCl. After acidification the reaction mixture is extracted with an organic solvent, for example, ether, dichloromethane or ethyl acetate. An inert atmosphere, such as a nitrogen gas atmosphere, is needed to recover the disubstituted indole (I) where $R_1$ and $R_2$ are OH.

In the case of the reductive cyclization of compounds in which $R_1$ and $R_2$ are acyloxy, such as, for example, acetoxy, the preferred reaction conditions for best yield are chosen so as to prevent deacylation of the compounds. The solvent for such cyclizations is a two-phase system. The two-phase solvent system limits interactions of the indole precursor with nucleophiles in the reaction medium. Useful two-phase systems include, for example, water/chloroform, water/carbon tetrachloride, water/ether or water/dichloromethane. The reaction is carried out in controlled acidic medium to prevent or limit nucleophilic attack by the dithionite ion. Preferably, a phosphate buffer of pH 4 is used. Other buffers which maintain the pH between about 4 and about 7 ion can also be used. Any water soluble metal dithionite salt is suitable. A water soluble zinc salt is added simultaneously in order to form zinc dithionite in situ. Zinc dithionite has a maximum reducing capacity at pH 4, whereas other dithionite salts, for example, sodium dithionite is active at pH higher than 7 but decomposes in slightly acidic media, e.g. at pH 4.

In the case of catechol compounds (dihydroxystyrenes), the same conditions as for diacyloxy-substituted compounds is applicable. However, an inert atmosphere is needed to prevent oxidation of the resulting 5,6-dihydroxy indole. It is also possible to carry out the catechol derivatives cyclization in a one phase aqueous system. The reaction may be carried out at a neutral pH, i.e. pH 7 or between pH 4–7. If the reaction is carried out at pH 7, it is not necessary to add a zinc salt to the reaction mixture.

When the nitrostyrene derivative is a dibenzyloxy derivative all of the reaction conditions mentioned above may be employed. Additionally, the pH of the reaction mixture may be alkaline. A zinc salt is not required if the reaction is carried out at neutral or alkaline pH and an inert atmosphere is not required.

Although the foregoing invention has been described in some detail by way of illustration and example for purposes of clarity of understanding, it will be obvious to those skilled in the art that certain changes and modifications may be practiced without departing from the spirit and scope thereof as described in the specification and as defined in the appended claims.

EXAMPLE 1

Synthesis of 5,6-dihydroxyindole

A mixture of 4,5-dihydroxy-2,β-dinitrostyrene (0.016 mol) in 65 ml 0.1 M phosphate buffer (pH 7) and a solution of $Na_2S_2O_4$ (10 eq.) in 65 ml of 0.1 M phosphate buffer (pH 7) were prepared. An inert gas was passed through into the mixture and the solution for 1 hour. The dithionite solution was then rapidly added to the 4,5-dihydroxy-2,β-dinitrostyrene solution and the stirred mixture was maintained in inert atmosphere for 20 minutes. The pH was adjusted to about 5 with 3 M HCl and the reaction was extracted with ethyl acetate in inert atmosphere. Combined organic layers were washed with saturated NaCl and dried over $Na_2SO_4$ in inert atmosphere. The solvent was concentrated under reduced pressure and at room temperature, and benzene was added to precipitate 5,6-dihydroxyindole. The product was obtained as a pale yellow solid in 40–45% yield (purity greater than 95%).

EXAMPLE 2

Nitration of a catechol compound

To a stirred mixture of 3,4-dihydroxy-β-nitrostryene (0.033 mol) and $ZnSO_4$ (5 eq.) in 200 ml of 0.1 M $NaHCO_3$ buffer, pH 8, and 40 ml of ethanol, at 0° C. (ice bath), a solution of tetranitromethane (1.5 eq.) in 80 ml ethanol was added dropwise. The mixture was then stirred in an ice bath for 35–40 min. Ethanol was removed under reduced pressure at room temperature; the aqueous mixture was acidified to pH 4 and extracted with ether (3×200 ml). The combined organic layers were washed with saturated NaCl and then dried over $Na_2SO_4$. The solvent was concentrated under reduced pressure and hexane was added to precipitate 4,5-dihydroxy-2,β-dinitrostyrene. The product was obtained as an orange solid, which was recrystallized from water, yielding 52% of 4,5-dihydroxy-2,β-dinitrostyrene as bright yellow needles.

EXAMPLE 3

Example 1 was repeated using 20 eq. $Na_2S_2O_4$; 10 eq. $ZnSO_4$; in 0.1 m phosphate buffer pH 4 and an inert nitrogen product. The cyclized product was obtained in 40% yield.

EXAMPLE 4

Example 1 was repeated using 20 eq. $Na_2S_2O_4$; 10 eq. $ZnS_2O_4$; 0.1 m phosphate buffer pH 4; methylene chloride in the aqueous medium; and an inert nitrogen atmosphere. The cyclized product was obtained in 40% yield.

EXAMPLE 5

Example 1 was repeated using 4,5-diacetoxy-2,β-dinitrostyrene (0.016 mol) 20 eq. $Na_2S_2O_4$; 0.1 M phosphate buffer pH 4 and methylene chloride in the reaction medium. A cyclized product was obtained in 65% yield.

EXAMPLE 6

Example 1 was repeated using 4,5-dibenzyloxy-2,β-dinitrostyrene (0.016 mol); 10 eq. $Na_2S_2O_4$; 12% v/v NH3; water/ethanol medium. A cyclized product in 75–78% yield was obtained.

EXAMPLE 7

Example 6 was repeated using 10 eq. $Na_2S_2O_4$. 0.1 M phosphate buffer pH 7 and ethanol medium. A cyclized product in 65% yield was obtained.

EXAMPLE 8

Example 6 was repeated using 20 eq. $Na_2S_2C_4$ 10 eq. $ZnSO_4$; 0.1 M phosphate buffer pH4 and ethanol medium. A cyclized product in 85–90% yield was obtained.

What is claimed is:

1. A process for preparing a compound of the formula (II):

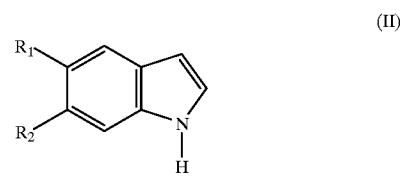

wherein $R_1$ and $R_2$ each independently denote hydrogen, lower acyloxy, benzyloxy or hydroxy with proviso that $R_1$ and $R_2$ are not both hydrogen, comprising subjecting a compound of the formula (I)

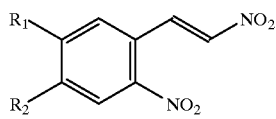

to a reductive cyclization in the presence of a dithionite salt.

2. The process of claim 1, further comprising isolating the compound of formula I.

3. The process of claim 1, wherein the dithionite salt is a water soluble salt.

4. The process of claim 1, wherein the reductive cyclization is carried out in the presence of a polar solvent or a biphasic solvent comprising water and a non-polar organic solvent.

5. The process of claim 1, wherein the dithionite is an alkali metal dithionite or an alkaline earth metal dithionite or zinc dithionite.

6. The process of claim 1, further comprising preparing the compound of formula I by reaction sequence:

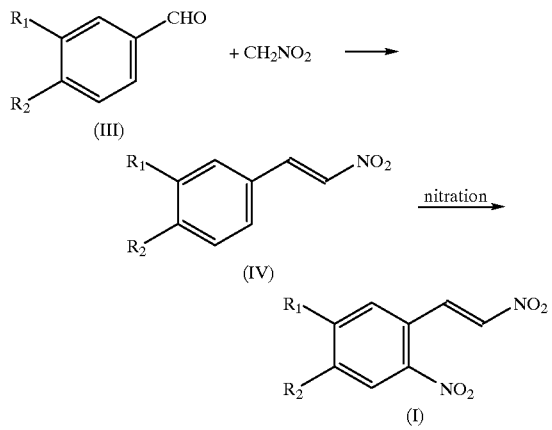

7. The process of claim 6, wherein $R_1$ and $R_2$ are hydroxy and the nitration is carried out in the presence of a zinc salt and the nitration agent is tetranitromethane.

8. The process of claim 6, wherein the reaction is carried out at an alkaline pH.

9. The process of claim 1, wherein $R_1$ and $R_2$ are each independently benzyloxy, acetoxy or hyroxy.

10. The process of claim 1, wherein $R_1$ and $R_2$ are benzyloxy.

11. The process of claim 10, wherein the reaction is carried out at pH between about 4 and 10.

12. The process of claim 1, wherein $R_1$ and $R_2$ are acetoxy.

13. The process of claim 12, wherein the reaction is carried out in a two-phase reaction medium comprising water and a non-polar organic solvent at a pH of between about 4 and about 7.

14. The process of claim 13, wherein the reaction is carried out using a mixture of water soluble metaldithionite salt and a water soluble zinc salt.

15. The process of claim 1, wherein $R_1$ and $R_2$ are hydroxy.

16. The process of claim 15, wherein the reaction is carried out in an inert atmosphere and at a pH of between about 4 and about 7.

17. The process of claim 16, wherein the reaction is carried out in a one phase aqueous system.

18. The process of claim 16, wherein the reaction is carried out using a mixture of a water soluble metal dithionite salt and a water soluble zinc salt.

19. The process of claim 5, wherein the dithionite salt is sodium dithionite.

* * * * *